United States Patent [19]

Romano et al.

[11] Patent Number: 4,849,387

[45] Date of Patent: Jul. 18, 1989

[54] CATALYST FOR THE SELECTIVE DECOMPOSITION OF CUMENE HYDROPEROXIDE AND PROCESS USING IT

[75] Inventors: Ugo Romano, Vimercate; Mario G. Clerici, San Donato Milanese; Giuseppe Bellussi, Piacenza; Franco Buonomo, San Donato Milanese, all of Italy

[73] Assignee: Enichem Sintesi S.p.A., Settimo, Italy

[21] Appl. No.: 112,462

[22] Filed: Oct. 26, 1987

Related U.S. Application Data

[62] Division of Ser. No. 854,527, Apr. 22, 1986, Pat. No. 4,743,573.

[30] Foreign Application Priority Data

Apr. 23, 1985 [IT] Italy ............................... 20458 A/85

[51] Int. Cl.$^4$ .......................... B01J 29/06; C07C 37/08
[52] U.S. Cl. ......................................... 502/64; 502/70; 568/385; 568/798
[58] Field of Search .................. 568/798, 385; 502/64, 502/79

[56] References Cited

U.S. PATENT DOCUMENTS

| | | | |
|---|---|---|---|
| 3,275,571 | 9/1966 | Mattox | 502/70 |
| 3,328,119 | 6/1967 | Robson | 502/64 |
| 3,531,397 | 9/1970 | Michalko | 502/70 |
| 4,299,733 | 11/1981 | Tu | 502/70 |
| 4,427,577 | 1/1984 | Koetsier | 502/66 |
| 4,490,566 | 12/1984 | Chang et al. | 568/798 |
| 4,594,332 | 6/1986 | Hoelderich et al. | 502/64 |

*Primary Examiner*—Mark L. Bell
*Assistant Examiner*—Anthony J. Green
*Attorney, Agent, or Firm*—Birch, Stewart Kolasch & Birch

[57] ABSTRACT

The present invention relates to a catalyst for the selective decomposition of cumene hydroperoxide, composed of zeolite crystals wherein a portion of the silicon atoms in the crystal lattice of silica is replaced by Al and B. The zeolite crystals are bonded to each other by a siliceous bonding agent which allows the catalyst to assume the shape of mechanically stable microspheres.

The invention relates also to a process in which the catalyst is used, and to the related operating conditions.

12 Claims, No Drawings

CATALYST FOR THE SELECTIVE DECOMPOSITION OF CUMENE HYDROPEROXIDE AND PROCESS USING IT

This application is a divisional of application Ser. No. 854,527, filed on Apr. 22, 1986, and now U.S. Pat. No. 4,743,573.

The present invention relates to a catalyst for the selective decomposition of cumene hydroperoxide and to a process using this catalyst.

In the synthesis of phenol and acetone, one of the methods used on an industrial scale is the synthesis of cumene from benzene and propylene, a subsequent peroxidation to cumene hydroperoxide, and an acid-catalyzed decomposition of the peroxide into phenol and acetone.

The decomposition of cumene hydroperoxide is generally carried out in the presence of $H_2SO_4$. This process leads to the formation of a mixture composed of: phenol, acetone, acetophenone and sulphonated by-products, the separation of which has a considerable effect on the production costs and on the complexity of the plant. It has now been surprisingly found that such a decomposition can be carried out with a higher conversion and selectivity to phenol and acetone, and without the drawbacks involved by the separation of $H_2SO_4$ and of its derivatives, by using a catalyst composed of zeolite crystals, wherein a portion of the silicon atoms of the crystal lattice of silica is replaced by Al and B. The zeolite crystals are bonded to each other by means of a siliceous bonding agent, which allows the catalyst to assume the shape of mechanically stable microspheres.

A first object of the present invention is to provide a catalyst for the selective decomposition of cumene hydroperoxide into phenol and acetone on the basis of silicon, aluminium and boron, wherein silicon, aluminium and boron, in the form of their oxides, constitute crystals having a structure of the zeolite type, wherein aluminium and boron replace silicon in the crystalline structure of silica, and the crystals are interconnected with each other by oligomeric silica.

The molar ratio between the silica of zeolite crystals and the oligomeric silica is within the range of from 80 to 95.

The catalyst according to the present invention is in the form of microspheres having dimensions ranging from 5 $\mu$m to 1000 $\mu$m, preferably from 20 $\mu$m to 100 $\mu$m.

The catalyst according to the present invention has the following general formula (after calcination at 550° C. and cooling to room temperature): 0.017–0.0025 $Al_2O_3.0.1$–$0.005$ $B_2O_3.SiO_2.0.2$–$0.5$ $H_2O$.

A second object of the present invention is to provide a method for the preparation of the above catalyst.

The catalyst is prepared by a two-step process, the first step of which is the preparation of the above zeolite crystals and the second of which is the interconnecting of the above zeolite crystals, by compounds able to form oligomeric silica.

The first step is accomplished by starting from alkyl silicates (alkyl groups of from 1 to 4 carbon atoms), in particular from tetramethyl- and/or tetraethylsilicate, possibly in aqueous solution, which are added to an alcoholic solution (aliphatic alcohol of from 1 to 6 carbon atoms) of an aluminium salt at a concentration of preferably from 4 to 5%, preferably an alcoholic solution of Al nitrate or acetate. The whole solution then is mixed with an aqueous solution of tetrapropylammonium hydroxide and $H_3BO$. From the reaction medium foreign cations, in particular cations of alkaline or alkaline-earth metals, must be absent.

The whole solution is heated under stirring to a temperature within the range of from 50° to 80° C., preferably to 60° C., for the purpose of hydrolyzing the alkyl silicate and removing an amount as high as possible of the alkyl alcohol obtained from the hydrolysis and of the alcohol coming from the solution of the aluminium salt.

After the hydrolysis of the alkyl silicate and the removal of alcohols, the resulting residual solution is charged into an autoclave equipped with a stirrer, and is heated, under its autogenous pressure, at a temperature of from 150° to 250° C., for a time period of from 3 hours to 10 days. A suspension of crystals is obtained. The crystals of the suspension are then separated from the the mother liquids, preferably by centrifuging, washed in deionized water and dried, preferably by centrifuging.

The second step consists in dispersing the above zeolite crystals in a clear solution obtained by hydrolyzing a tetraalkyl silicate (alkyl group of from 1 to 4 carbon atoms), preferably tetramethyl- or tetraethyl-silicate, in an aqueous solution of tetraalkylammonium (TAA) hydroxide (alkyl group of from 1 to 5 carbon atoms) for a time of from 1 to 2 hours at a temperature of 60°–70° C.

The suspension obtained is atomized, preferably by means of a spray drier, and microspheres having an average diameter of from 5 to 1000 $\mu$m, preferably of from 20 to 100 $\mu$m, are obtained.

The microspheres are then calcined at a temperature of from 500° to 600° C., preferably at 550° C. for 2–10 hours, preferably for 5 hours.

The reaction mixture for the synthesis of the zeolite has the following molar composition: 0.1–0.35 $(TPA_2)O$; $SiO_2$; 0.0025–0.01 $Al_2O_3$; 0.2–0.02 $B_2O_3$; 20–40 $H_2O$. $(TPA_2)O$ = tetrapropylammonium hydroxide.

The reaction mixture for the preparation of the catalyst has the following composition by mole (with the exclusion of $Al_2O_3$ and $B_2O_3$): 0.05–0.15 $(TAA)_2O$; 4–19 $SiO_2$ (of zeolite); 1 $SiO_2$ (of tetraalkyl silicate); 80–600 $H_2O$.

A third object of the present invention is to provide a method for the selective decomposition of cumene hydroperoxide into phenol and acetone using the above catalyst.

The method according to the present invention consists in contacting cumene hydroperoxide with the catalyst, preferably placed inside a reactor on one or more stationary or fluidized beds at a temperature of from 20° to 120° C., preferably of 40°–60° C., and in discharging the reaction products and undecomposed cumene hydroperoxide. Cumene hydroperoxide can be supplied as such, or diluted in a suitable solvent and, in particular, cumene.

The space speed LHSV referred to cumene hydroperoxide in the case of continuous operating is between 0.5 and 10 $h^{-1}$. For the batchwise operation, the permanence time is within the range of from 1' to 120', preferably of 15 min.–20 min.

Some Examples having the purpose of better illustrating the invention shall be now set forth. The specific examples are in no way intended to limit the scope of the present invention.

EXAMPLE NO. 1

An amount of 67.8 g of $Al(NO_3)_3.9H_2O$ is dissolved in 1275 g of ethyl alcohol and to these compounds, under stirring, 2819 g of tetraethyl-silicate is added, with stirring being continued until a homogeneous and clear solution is obtained.

Into a stainless steel vessel 1036 g of deionized water, 8878 g of an aqueous solution at 15.5% by weight of tetrapropyl-ammonium (TPA+) hydroxide and 167.5 g of powder of boric acid are added sequentially and under stirring. When the acid has been completely dissolved, to this solution the previously obtained solution is added, and the mixture is stirred while being heated at 60° C. for about 4 hours and in any case until the hydrolysis of the silicate is completed, and the present ethyl alcohol has been nearly completely removed. The molar composition of the reaction mixture is the following:

$SiO_2/Al_2O_3 = 150$; $SiO_2/B_2O_3 = 10$; $TPA^+/SiO_2 = 0.5$; $H_2O/SiO_2 = 35$.

The so-obtained solution is charged into an autoclave equipped with a stirrer and is heated under its autogenous pressure under stirring for 4 hours at 170° C. The discharged product is centrifuged and the cake is accurately dispersed in 70 liters of deionized water, and the obtained suspension is again centrifuged, yielding a washed cake.

An amount of 2451 g of tetraethylsilicate is hydrolyzed in the presence of 216 g of a solution at 15.5% of tetrapropyl-ammonium hydroxide and 1300 g of deionized $H_2O$. The washed cake discharged from the centrifuge is accurately dispersed into the so-obtained clear solution, until a milky suspension is obtained. Such suspension is fed to a spray dryer and atomized so as to obtain microspheres having an average diameter within the range of from 10 to 30 μm. The product is calcined for 1 h and 30 min. under $N_2$, with the temperature being raised from room temperature to 550° C., and then at a constant temperature of 550° C. in air for an additional 4 hours. The finished catalyst (A) is thus obtained, the chemical analysis of which is as follows:

$SiO_2$: 96.87; $Al_2O_3$: 1.851; $B_2O_3$: 1.029; $H_2O$; balance to 100.

To 50 g of a phenol/acetone (50% by mole) solution, kept at a temperature controlled at 40° C., 3 g of catalyst A and then 17 g of cumene hydroperoxide are added. The decomposition is monitored by iodimetric titration and gas-chromatographic analysis.

The results are reported in Table 1.

EXAMPLE NO. 2

Following the procedure as disclosed in Example 1, the washed cake discharged from the centrifuge is obtained. The solid is calcined under $H_2$ with the temperature being raised from room temperature to 550° C. and then at a constant temperature of 550° C. in air for 4 hours.

The product obtained (B) has the following chemical composition:

$SiO_2$: 96.93; $Al_2O_3$: 1.968; $B_2O_3$: 0.852; $H_2O$: balance to 100.

By the reactants and procedures as disclosed in Example 1, with the exception that 3 g of catalyst B is used in lieu of the 3 g of catalyst A, the results described in Table 1 are obtained.

EXAMPLE NO. 3 (COMPARISON)

Into a 100-cc beaker, 1 g of $Al(NO_3)_3.9H_2O$ is dissolved in 18.8 g of anhydrous $C_2H_5OH$ and to the solution obtained, 41.6 g of tetraethyl-silicate is added.

Into another vessel of pyrex glass, 15.3 g of $H_2O$, 131 g of aqueous solution of tetrapropyl-ammonium hydroxide at 15.5% by weight and the previously prepared alcoholic solution are added under stirring. The whole solution is heated at 60° C. under stirring for about 4 hours, and in any case until the hydrolysis of the silicate has ended and ethyl alcohol has been nearly completely removed. The solution obtained, which has the following molar composition: $SiO_2/Al_2O_3 = 150$; $TPA^+/SiO_2 = 0.5$; $H_2O/SiO_2 = 35$, is charged into an autoclave equipped with a stirrer and heated under stirring, under its autogenous pressure, at 170° C. for 4 hours.

The discharged milky suspension is centrifuged, the cake is dispersed in 500 g of deionized water and the suspension is centrifuged. The washed cake is then calcined by increasing the temperature, over 1 h and 30 min. under $N_2$, from room temperature to 550° C. and then at a constant temperature of 550° C. in air for 4 hours. The product obtained (C) has the following composition:

$SiO_2$: 96.58; $Al_2O_3$: 1.077; $H_2O$: balance to 100.

By the reactants and procedures as disclosed in Example 1, with the exception that 3 g of catalyst C is used in lieu of the 3 g of catalyst A, the results described in Table 1 are obtained.

EXAMPLE NO. 4 (COMPARISON)

Into a 300-cc beaker of pyrex glass, 131 g of an aqueous solution of tetrapropyl-ammonium hydroxide at 15.5% by weight, 15.3 of deionized $H_2O$, and 2.5 g of $H_3BO_3$ are added under stirring. The whole solution is stirred, with heating if necessary, until a clear solution is obtained, and then 41.6 g of tetraethyl-silicate is added, always under stirring. The stirring is continued for 4 hours while heating at 60° C., and anyway until the complete hydrolysis of the silicate has occurred, and to the nearly total removal of ethyl alcohol. The solution obtained, which has the following molar composition:

$SiO_2/B_2O_3 = 10$; $TPA^+/SiO_2 = 0.5$; $H_2O/SiO_2 = 35$, is charged into an autoclave equipped with a stirrer and heated under stirring, under its autogenous pressure, at 170° C. for 4 hours.

The discharged milky suspension is centrifuged, the cake is dispersed in 500 g of deionized water, and the suspension is centrifuged. The washed cake is then calcined by increasing the temperature, over 1 h and 30 min., under $N_2$, from room temperature to 550° C. and then at a constant temperature of 550° C. in air for 4 hours. The product obtained (D) has the following composition:

$SiO_2$: 97.55; $B_2O_3$: 1.954; $H_2O$: balance to 100.

By the reactants and procedures as disclosed in Example 1, with the exception that 3 g of catalyst D is used in lieu of the 3 g of catalyst A, the results described in Table 1 are obtained.

EXAMPLE NO. 5

By the procedure and reactants as disclosed in Example 1, the decomposition of cumene hydroperoxide (CHP) is carried out by using, in lieu of the 3 g of catalyst A, 0.2 g of catalyst E (sulphuric acid in aqueous solution at 96%) and adjusting the addition rate of CHP so that the addition takes place within a time of 10'; the temperature is always kept at 40° C. After a total time of 30 min. the reaction mixture is neutralized by sodium bicarbonate, and analyzed by iodimetric titration and gas-chromatographic analysis.

The results are reported in Table 1.

TABLE 1

| CATA-LYST | REACTION TIME | CHP % CONV. | % SELECTIVITY PHENOL | % SELECTIVITY ACETOPHENONE | OTHERS |
|---|---|---|---|---|---|
| A | 15 min. | 100 | 96% | 3% | 1% |
| B | 20 min. | 100 | 96% | 3% | 1% |
| C | 120 min. | 80 | 85.5% | 8% | 6.5% |
| D | 120 min. | 40 | 80.5% | 12.2% | 7.8% |
| E | 30 min. | 100 | 95% | 3% | 2% |

An example of continuous synthesis of phenol and acetone is now presented.

A test is carried out by operating continuously by using equipment consisting of a glass reactor of 0.5 l in volume, equipped with mechanical stirring means, automatic level control, temperature control system, inlet for the cumene hydroperoxide solution, outlet for the outflowing stream, and equipped with a filtering candle to avoid loss of the catalyst.

To exemplify the purpose, a test carried out at 60° C., by feeding a solution of CHP (84%) in cumene at the flow rate of 0.1 l/h, with a reactants volume in the reactor of 0,12 l, 7 g of catalyst A, is described. The reaction is monitored by means of iodimetric titration and gas-chromatographic analysis of samples drawn at regular time intervals.

The conversion of cumene hydroperoxide, after 10 hours of operation, is 90%, with the effluent having the following composition (% by weight), with the exclusion of cumene:

CHP, 10%
Phenol, 54.2%
Acetone, 33.3%
Acetophenone, 1.3%
Others, 1.0%

The yields referred to CHP are generally higher than 98%.

In regards to the catalyst, at the end of the test, it still has the same initial characteristics, apart from a light brown color.

It can be totally reactivated either by washing at high temperature (100°-150° C.) with methanol or with another suitable solvent, or by calcination at 550° C. in air.

When it is used again after these treatments, it displays a behavior identical to that of a sample of a just prepared catalyst.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for the selective decomposition of cumene hydroperoxide into phenol and acetone, which comprises contacting cumene hydroperoxide with a catalyst at a temperature of from 20° to 120° C., wherein said catalyst comprises oxide forms of silicon, aluminum, and boron constituting crystals having a structure of zeolite, wherein aluminum, and boron replace silicon in the crystalline structure of silica, and the crystals are interconnected with each other by oligomeric silica.

2. The method according to claim 1, wherein cumene hydroperoxide is contacted with the catalyst at a temperature of from 40° to 60° C.

3. The method according to claim 1, wherein the molar ratio of the silica of zeolite crystals to the oligomeric silica is within the range of from 80 to 95.

4. The method according to claim 1, wherein said catalyst is in the form of microspheres having diameters within the range of from 5 to 1000 $\mu$m.

5. A method for the selective decomposition of cumene hydroperoxide into phenol and acetone, which comprises (a) contacting cumene hydroperoxide with a catalyst placed in a reaction system at a temperature of from 20° to 120° C., wherein said catalyst comprises oxide forms of silicon, aluminum, and boron constituting crystals having a structure of zeolite, wherein aluminum and boron replace silica in the crystalline structure of silica, and the crystals are interconnected with each other by oligomeric silica; and (b) discharging phenol, acetone, and undecomposed cumene hydroperoxide from said reaction system.

6. The method according to claim 5, wherein said reaction system is a reactor or a fluidized bed.

7. The method according to claim 5, wherein cumene hydroperoxide is contacted with said catalyst at a temperature of from 40° to 60° C.

8. The method according to claim 5, wherein said cumene hydroperoxide which is contacted with said catalyst is diluted in a solvent.

9. The method according to claim 8, wherein said solvent is cumene.

10. The method according to claim 5, which is conducted batchwise in a time of from 1 minute to 2 hours.

11. The method according to claim 10, which is conducted batchwise in a time of from 15 minutes to 20 minutes.

12. The method according to claim 5, which is conducted continuously at a space speed LHSV in reference to cumene hydroperoxide of between 0.5 and 10 $h^{-1}$.

* * * * *